US00PP36702P2

(12) United States Plant Patent
Elstgeest

(10) Patent No.: US PP36,702 P2
(45) Date of Patent: May 20, 2025

(54) ***DIEFFENBACHIA* PLANT NAMED 'DIFMUMRS23'**

(50) Latin Name: *Dieffenbachia seguine*
Varietal Denomination: DIFMUMRS23

(71) Applicant: Elstgeest Young Plants B.V., Rijsenhout (NL)

(72) Inventor: Debbie Elstgeest, Rijsenhout (NL)

(73) Assignee: Elstgeest Young Plant Holdings B.V., Rijsenhout (NL)

( * ) Notice: Subject to any disclaimer, the term of this patent is extended or adjusted under 35 U.S.C. 154(b) by 0 days.

(21) Appl. No.: 18/831,346

(22) Filed: Nov. 25, 2024

(30) Foreign Application Priority Data

Nov. 27, 2023 (QZ) ..... PBR 2023/2534

(51) Int. Cl.
*A01H 5/12* (2018.01)
*A01H 6/10* (2018.01)

(52) U.S. Cl.
USPC ..... Plt./378
CPC ..... *A01H 6/10* (2018.05)

(58) Field of Classification Search
USPC ..... Plt./378
CPC ..... A01H 5/12; A01H 5/02; A01H 5/00
See application file for complete search history.

*Primary Examiner* — Kent L Bell
(74) *Attorney, Agent, or Firm* — Samuel R. McCoy, Jr.

(57) ABSTRACT

'DIFMUMRS23' is a new and distinctive *Dieffenbachia* plant which is characterized by a larger stature growth habit with numerous freely-branching main shoots, a relative abundance of large ovate foliage, light yellow foliage veins, light yellow-green foliage that is marbled and blotched green to yellow-green towards the margins, with green foliar margins that become progressively broader with age, and the stability of all characteristics from generation to generation.

3 Drawing Sheets

Latin name of the genus and species: The Latin name of the genus and species of the novel variety disclosed herein is *Dieffenbachia seguine*.

Variety denomination: The inventive variety of *Dieffenbachia* disclosed herein has been given the variety denomination 'DIFMUMRS23'.

CROSS REFERENCE TO RELATED APPLICATIONS

This application claims priority to the Community Plant Variety Rights application number 2023/2534, filed Nov. 27, 2023, which is herein incorporated by reference.

BACKGROUND OF THE INVENTION

Parentage: 'DIFMUMRS23' originated as a naturally-occurring, whole plant mutation of *Dieffenbachia seguine* 'MARS' (not patented). In August of 2019 the inventor discovered the mutation at a commercial greenhouse in Rijsenhout, the Netherlands, growing amongst a crop of *Dieffenbachia* 'MARS'. The mutation was noted for its freely-branching, compact growth habit and was subsequently isolated for further evaluation in order to confirm the distinctness and stability of the characteristics first observed. Upon confirmation of distinctness and stability, the new *Dieffenbachia* plant was selected for commercialization and given the name 'DIFMUMRS23'.

Asexual Reproduction: Asexual reproduction of 'DIFMUMRS23', by way of softwood stem cuttings, was first performed in the August of 2019 at a commercial greenhouse in Rijsenhout, the Netherlands. Five successive generations so produced have shown that the unique features of the instant cultivar are stable and reproduced true to type.

SUMMARY OF THE INVENTION

The cultivar 'DIFMUMRS23' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Dieffenbachia* cultivar 'DIFMUMRS23'. These traits, in combination, distinguish 'DIFMUMRS23' as a new and distinct cultivar.

1. *Dieffenbachia* 'DIFMUMRS23' exhibits a larger stature growth habit with numerous freely branching main shoots; and
2. *Dieffenbachia* 'DIFMUMRS23' exhibits a relative abundance of large ovate foliage; and
3. *Dieffenbachia* 'DIFMUMRS23' exhibits foliar veins with a light yellow general coloration; and
4. *Dieffenbachia* 'DIFMUMRS23' exhibits light yellow-green foliage that is marbled and blotched green to yellow-green towards the margins, with green foliar margins that become progressively broader with age.

BOTANICAL DESCRIPTION OF THE PLANT

Figure 1:
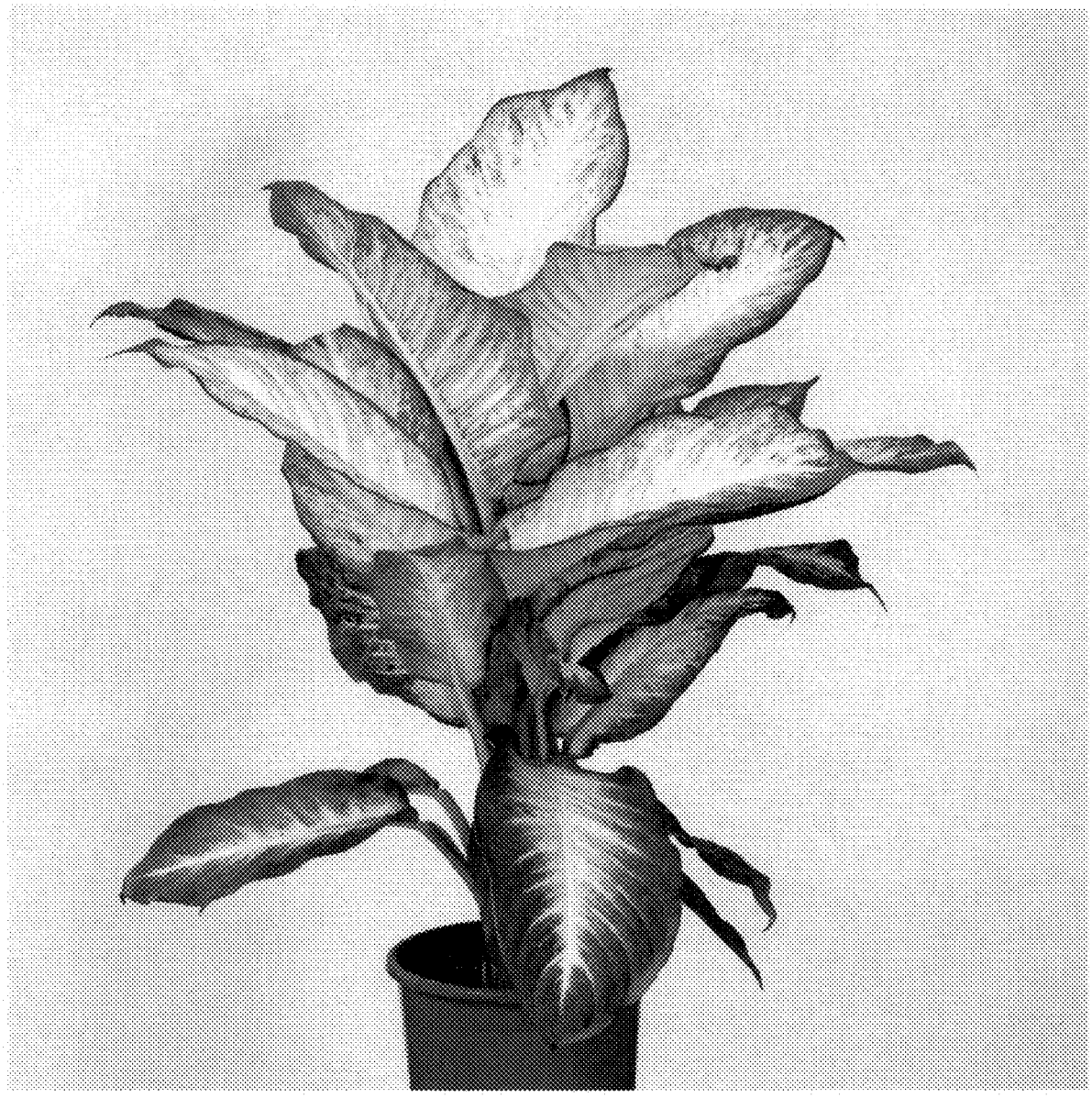
FIG. 1 shows, as nearly true as it is reasonably possible to make the same in color illustrations of this type, an exemplary 'DIFMUMRS23' plant at approximately 35 weeks old, potted into a 21 cm nursery container, grown in a greenhouse in Rijsenhout, The Netherlands.
Figure 2:
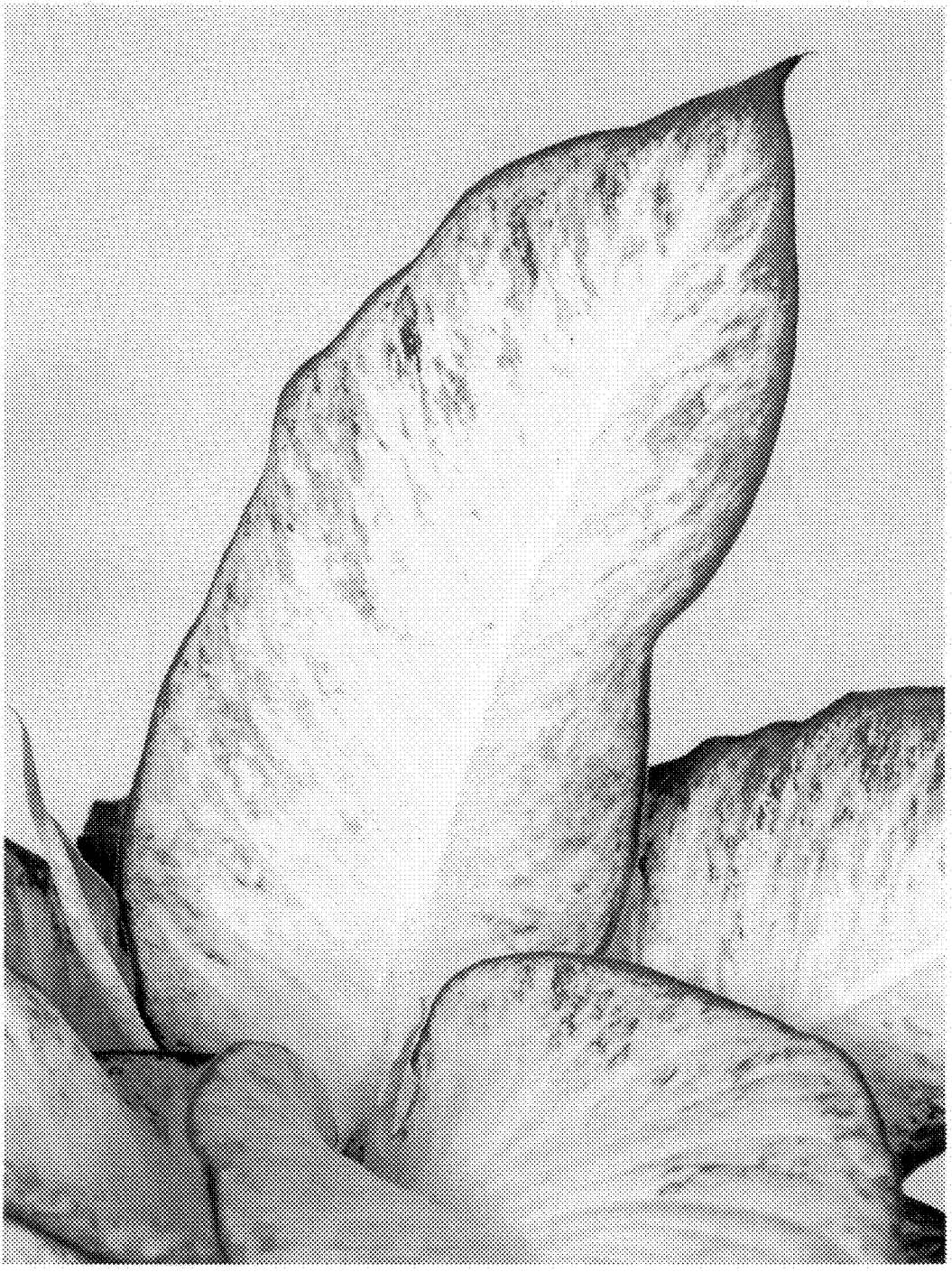
FIG. 2 shows, as nearly true as it is reasonably possible to make the same in color illustrations of this type, the typical juvenile foliage of 'DIFMUMRS23'.
Figure 3:
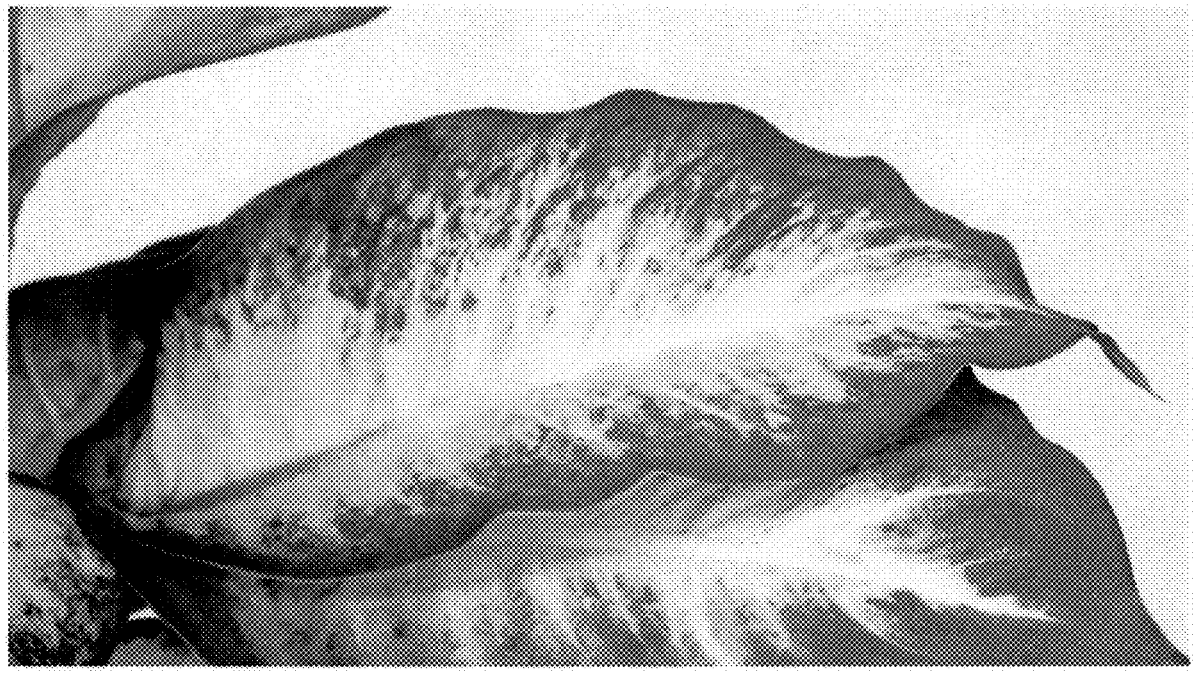
FIG. 3 shows, as nearly true as it is reasonably possible to make the same in color illustrations of this type, the typical mature foliage of 'DIFMUMRS23'.

The following is a detailed botanical description of a new and distinct variety of *Dieffenbachia* known as 'DIFMUMRS23', based upon observations of plants, approximately 24 weeks old from a rooted cutting, grown in 17 cm nursery container in a climate-controlled greenhouse in Rijsenhout, the Netherlands. Observation data was recorded in November 2023. Plants were produced using conventional greenhouse production protocols for *Dieffenbachia* which consisted of regular 2.2 to 2.5 EC fertilizer applications and regular ebb and flow (i.e. flood bench) irrigation. No pest or disease control measures were utilized in production. Plants were produced under 50 percent shade and no photoperiodic treatments or artificial light was given to the plants.

Those skilled in the art will appreciate that certain characteristics of the variety 'DIFMUMRS23' will change with time as the plant develops. The variety has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 edition.

A botanical description of 'DIFMUMRS23' and comparisons with the parent and the most similar variety of common knowledge are provided below.

General plant description:

*Growth habit*.—Clump forming; large stature perennial.

*Plant form*.—Obovate.

*Growth rate*.—Moderately fast growing.

*Plant vigor*.—Moderately to highly vigorous.

*Height*.—56.8 cm.

*Width*.—55.7 cm.

*Propagation*.—Softwood stem cuttings.

*Time to initiate roots*.—Approximately 20 days to initiate roots at approximately 21 degrees Celsius.

*Time to produce a finished plant*.—Approximately 35 weeks.

*Environmental tolerances*.—USDA Zones 10 to 12; at least tolerant of temperatures of up to 40 degrees Celsius. Moderate tolerance to rain inundation; low to moderate tolerance to wind.

*Pest and pathogen resistance and susceptibility*.—Plants have been observed to be similarly susceptible and resistant to pathogens and pests common to *Dieffenbachia*.

Root system:

*General*.—Slightly fibrous and fleshy; moderately freely branched, and moderately dense.

*Length of primary roots*.—Unable to determine in observation.

*Diameter of primary roots*.—Unable to determine in observation.

*Color*.—Yellow-white, nearest to a combination of RHS 158C and 158D.

*Texture*.—Smooth.

Stems:

*Branching habit*.—Basal branching with few lateral branches.

*Number of main shoots per plant*.—4.

*Number of lateral branches per plant*.—1.

*Appearance; cross-section*.—Rounded.

*Length of main shoots*.—21.5 cm.

*Diameter of main shoots*.—2.2 cm.

*Internode length on main shoots*.—3.3 cm.

*Aspect*.—Upright averaging at 0-degrees from vertical.

*Strength*.—Strong.

*Color, juvenile*.—Yellow-green, nearest to RHS 145A.

*Color, mature*.—Green, nearest to RHS 137B; marbled with yellow-green, nearest to RHS 147C.

*Color at internodes*.—Green, nearest to RHS 137B; marbled with yellow-green, nearest to 147C.

Foliage:

*Arrangement*.—Alternate.

*Division*.—Simple.

*Quantity of leaves per lateral branch*.—Average of 7.

*Leaf shape*.—Ovate.

*Leaf apex*.—Apiculate.

*Leaf base*.—Truncate.

*Aspect*.—Slightly carinate.

*Attitude*.—Upward and outward.

*Leaf length*.—Average 29.3 cm.

*Leaf width*.—Average 13.8 cm.

*Leaf margin*.—Entire; moderately undulated.

*Texture, adaxial surface*.—Glabrous, smooth, and slightly glossy.

*Texture, abaxial surface*.—Glabrous, smooth, and slightly glossy.

*Juvenile color, adaxial surface*.—Yellow-green, nearest to a blend of RHS 145D and 150D, and fading slightly darker distally from the main vein, nearest to a combination of 145C and 150C. The lamina is marbled and blotched green to yellow-green towards the margins, nearest to a combination of RHS 143A, 143B, 144B, and 145A; margins of the lamina are green, nearest to 137B.

*Juvenile color, abaxial surface*.—Yellow-green, nearest to a blend of RHS 145D and 150D, and fading slightly darker distally from the main vein, nearest to a combination of 145C. The lamina is marbled and blotched green to yellow-green towards the margins, nearest to RHS 143A, 144A, 144B, and 144C; margins of the lamina are green, nearest to 138A.

*Mature color, adaxial surface*.—Yellow-green, a blend closest to RHS N144D and 145A, the lamina is marbled and speckled with green distally from the main vein, nearest to N137A and N137C. The lamina margins are green, nearest to RHS NN137A.

*Mature color, abaxial surface*.—Yellow-green, nearest to RHS 145B. The lamina is specked with blotches of green distally from the main vein with green to yellow-green, nearest to RHS 138A and 147B. The lamina broad margins are green to yellow-green, closest to a blend of RHS 138A and 147B.

*Venation*.—Vein pattern — Pinnate. Vein color, adaxial surface — Yellow-green to white, nearest to a mixture of RHS 150D and 155A. The proximal portion of the main vein is heavily suffused with green, nearest to RHS 137A. Vein color, abaxial surface — Yellow-green to white, nearest to a mixture of RHS 150D and 155A.

*Petiole*.—Length — Approximately 11.2 cm. Diameter — The adaxial surface of the petiole is flattened; average width is 0.8 cm; average height is 1.4 cm. Texture and luster — Glabrous, smooth, and matte. Color, adaxial surface — Green-white, nearest to RHS 157A. Color, abaxial surface — Yellow-green, nearest to RHS 145B to 145D. Strength — Strong. Geniculum — None present. Petiole wings — None present.

Inflorescence: No flowers observed to date.

Flower bud: No flowers observed to date.

Flower: No flowers observed to date.

Reproductive organs: No flowers observed to date.

Seed and fruit: No flowers observed to date.

COMPARISONS WITH THE PARENT

Plants of the new cultivar 'DIFMUMRS23' differ from its parent, *Dieffenbachia seguine* 'MARS', by the characteristics described in Table 1.

COMPARISON BETWEEN 'DIFMUMRS23' AND 'MARS'

TABLE 1

| Characteristics | 'DIFMUMRS23' | 'MARS' |
|---|---|---|
| Quantity of main shoots. | More main shoots than 'MARS'. | Less main shoots than 'DIFMUMRS23'. |
| Growth habit. | More compact than 'MARS'. | Less compact than 'DIFMUMRS23'. |
| General coloration of the mature adaxial foliar surface. | Light yellow-green, and marbled and blotched green to yellow-green towards the margins; broadly margined green. | Dark green and sparsely and irregularly blotched light yellow-green at and near the main vein and proximal portions of lateral veins. |

COMPARISONS WITH THE MOST SIMILAR VARIETY OF COMMON KNOWLEDGE

Plants of the new cultivar 'DIFMUMRS23' may be distinguished from the commercial variety *Dieffenbachia* 'REEVA' (U.S. Plant Pat. No. 29,666) by the combination of characteristics described in Table 2.

COMPARISON BETWEEN 'DIFMUMRS23' AND 'REEVA'

TABLE 2

| Characteristics | 'DIFMUMRS23' | 'REEVA' |
|---|---|---|
| Lamina size. | Smaller in size than 'REEVA'. | Larger in size than 'DIFMUMRS23'. |
| Growth habit. | More compact than 'REEVA' with a taller canopy of leaves growing from main and lateral shoots uniformly. | Less compact than 'DIFMUMRS23' with a more variation in shoot height. |
| General coloration of the juvenile adaxial foliar surface. | Light yellow-green, and marbled and blotched green to yellow-green towards the margins; narrowly margined green. | Dark green and centrally and irregularly blotched light yellow-green. |
| General coloration of the mature adaxial foliar surface. | Light yellow-green, and marbled and blotched green to yellow-green towards the margins; broadly margined green. | Dark green and centrally and irregularly blotched light yellow-green. |

That which is claimed is:

1. A new and distinct variety of *Dieffenbachia* plant named 'DIFMUMRS23', substantially as described and illustrated herein.

* * * * *